United States Patent
Boykin et al.

(10) Patent No.: US 6,486,200 B1
(45) Date of Patent: Nov. 26, 2002

(54) PRODRUGS FOR ANTIMICROBIAL AMIDINES

(75) Inventors: David W. Boykin, Atlanta, GA (US); M. Syed Rahmathullah, Mississauga (CA); Richard R. Tidwell, Pittsboro, NC (US); James E. Hall, Chapel Hill, NC (US)

(73) Assignees: The University of North Carolina at Chapel Hill, Chapel Hill, NC (US); Georgia State University Research Foundation, Inc., Atlanta, GA (US)

( * ) Notice: Subject to any disclaimer, the term of this patent is extended or adjusted under 35 U.S.C. 154(b) by 0 days.

(21) Appl. No.: 09/612,138

(22) Filed: Jul. 7, 2000

Related U.S. Application Data

(60) Provisional application No. 60/142,829, filed on Jul. 8, 1999.

(51) Int. Cl.[7] .................... A61K 31/357; C07D 317/14

(52) U.S. Cl. ................... 514/467; 514/473; 549/448; 549/450; 549/451

(58) Field of Search ................ 514/467, 473; 549/448, 449, 450, 457, 478

(56) References Cited

U.S. PATENT DOCUMENTS

| | | | | |
|---|---|---|---|---|
| 4,748,265 A | * | 5/1988 | Oxbol et al. ................ | 560/25 |
| 5,103,041 A | * | 4/1992 | A'Court et al. ............. | 560/132 |
| 5,260,473 A | * | 11/1993 | McGhee et al. ............. | 558/260 |
| 5,618,827 A | * | 4/1997 | Oxford ....................... | 514/326 |
| 5,668,166 A | * | 9/1997 | Tidwell et al. .............. | 514/411 |
| 5,723,495 A | * | 3/1998 | Hall et al. .................. | 514/633 |
| 5,843,980 A | * | 12/1998 | Hall et al. .................. | 514/438 |

FOREIGN PATENT DOCUMENTS

| | | | |
|---|---|---|---|
| EP | 0051871 A1 | * 5/1982 | ....... C07C/125/065 |
| EP | 0142670 B1 | * 5/1985 | ......... C07C/269/00 |
| WO | WO 85/05105 | 11/1985 | ......... C07D/285/00 |
| WO | WO 97/17949 | 5/1997 | ......... A61K/31/155 |
| WO | WO 97/23499 | 7/1997 | ........... C07K/5/00 |

OTHER PUBLICATIONS

Bundgaard; *Design of prodrugs*, Elsevier Science Piblishers B.V. (Biomedical Division), The Netherlands, ISBN 0–444–80675–X, pp. 1–92 (1985).*

Bundgaard et al.; *A Textbook of Drug Design and Development*, Harwood Academic Publishers GmbH, Switzerland, ISBN 3–7186–5099–1, pp. 113–191 (1991).*

Friis et al.; *A Textbook of Drug Design and Development Second Edition*, Harwood Academic Publishers GmbH, The Netherlands, ISBN 3–7186–5866–6, pp. 351–385 (1996).*

Adams et al.; "Synthesis and Antitumor Activity of 9–[(Carbamoyloxy)alkyl]anthracyclines: A Novel Class of Anthracycline Derivatives," *J. Med. Chem.* 33:9 2380–2384 (1990).*

Alexander et al.; "(Acyloxy)alkyl Carbamate Prodrugs of Norfloxacin," *J. Med. Chem.* 34:1 78–81 (1991).*

Alpegiani et al.; "On the Preparation of 4–Hydroxymethyl–5–Menthyl–1,3–Dioxol–2–One," *Synthetic Communications* 22:9 1277–1282 (1992).*

Bajic et al.; "Synthesis of 2,5–Bis–(4–Cyanophenyl)–Furan,"2:135–140 (1996).*

Boykin et al.; "Anti–Pneumocystis Activity of Bis–Amidoximes and Bis–O–Alkylamidoximes Prodrugs," *Bioorganic & Medical Chemistry Letters* 6:24 3017–3020 (1996).*

(List continued on next page.)

*Primary Examiner*—Robert W. Ramsuer
*Assistant Examiner*—Golam M. M. Shameem
(74) *Attorney, Agent, or Firm*—Jenkins & Wilson, P.A.

(57) ABSTRACT

A methods of treating an infection comprises administering a therapeutically effective amount of a compound described by the Formula (I):

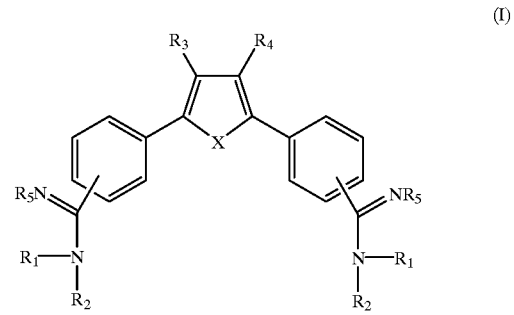

wherein:

X may be O, S, or NR' wherein R' is H or loweralkyl;

$R_1$ and $R_2$ may be independently selected from the group consisting of H, loweralkyl, oxyalkyl, alkoxyalkyl, cycloalkyl, aryl, hydroxyalkyl, aminoalkyl, and alkylaminoalkyl;

$R_3$ and $R_4$ are each independently selected from the group consisting of H, loweralkyl, halogen, oxyalkyl, oxyaryl, and oxyarylalkyl;

$R_5$ is represented by a formula selected from the group consisting of:

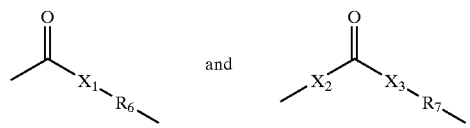

wherein:

$X_1$, $X_2$, and $X_3$ are independently selected from O and S; and $R_6$ and $R_7$ are independently selected from the group consisting of loweralkyl, aryl, alkylaryl, oxyaryl, an ester-containing substituent, and oxyalkyl; or a pharmaceutically acceptable salt thereof.

6 Claims, 1 Drawing Sheet

OTHER PUBLICATIONS

Boykin et al.; "Dicationic Diaryfurans as Anti-*Pneumocystis carinii* Agents," *J. Med. Chem.* 38 912–916 (1995).

Das et al,; "Synthesis and Antiprotozoal Activity of 2,5–Bis(4–guanylphenyl)furans," *Journal of Medicinal Chemistry* 20:4 531–536 (1977).

Hertnarski et al.; "Preparation and Properties of Phenyl Carbamates with Phosphoryl and Carbamyl Substituents," *J. Agr. Food Chem.* 20:3 543–546 (1972).

Koreeda et al.; "A New Reagent for the Selective, High–Yield N–Delkylation of Tertiary Amines: Improved Syntheses of Naltrexone and Nalbuphine," *J. Org. Chem.* 49:11 2081–2082 (1984).

Kumar et al.; "Anti-*Pneumocystis carinii* pneumonia activity of dicationic 2, 4–diarylpyrimidines," *Eur. J. Med. Chem.* 31 767–773 (1996).

Kasukawa et al.;"N–(3,4–Methylenedioxyphenyl)carbamates as Potent Flower–Inducing Compounds in *Asparagus* Seedlings as Well as Probes for Binding to Cytocrome P–450," *Z. Naturforsch* 50:c 373–379 (1995).

Lin et al.; "Mono and Bis Double Ester Prodrugs of Novel Aminomethyl–THF 1–Methylcarbapenenems," *Bioorganic & Medicinal Chemistry Letters* 7:14 1811–1816 (1997).

Lombardy et al.;"Synthesis and DNA Interactions of Benzimidazole Dications Which Have Activity against Opportunistic Infections," *J. Med. Chem.* 39 1452–1462 (1996).

Millan et al.; "The Dealkylation of Tertiary Aliphatic Amines with Phenyl Chlorothionoformate," *Tetrahedron Letters* 39 4387–4390 (1998).

Sakamoto et al.; "Studies on Prodrugs. II. Preparation and Characterization of (5–Substituted 2–Oxo–1, 3–dioxolen–4–yl)methyl Esters of Ampicillin," *Chem. Pharm. Bull.* 32:6 2241–2248 (1984).

Shridhar et al.; "Synthesis of Some New Carbamates & Amidines Derived from –Amino–$_3$–N,N–disubstitutedamino/heterocyclyl–$_2$H–$_{1,4}$–behzoaxazines as Possible Anthelmintics," *Indian Journal of Chenistry* 20 :B 1075–1077 (1981).

Thomsen et al.; "Evaluation of phenyl carbamates of ethyl diamines as cylization–activated prodrug forms for protecting phenols against first–pass metabolism," *International Journal of Pharmaceutics* 112 143–152 (1994).

Thomsen et al.; "Cyclization–activated phenyl carbamate prodrug forms for protecting phenols against first–pass metabolism," *International Journal of Pharmaceutics* 91 39–49 (1993).

Tidwell et al.; "Activity of Cationically Substituted Bis–Benzimidazoles against Experimental *Pneumocystis carinii* Pneumonia," *Antimicrobial Agents and Chemotheraoy* 37:8 1713–1716 (1993).

Weller et al.; "Orally Active Fibrinogen Receptor Antagonists. 2. Amidoximes as Prodrugs of Amidines," *J. Med. Chem.* 39:16 3139–3147 (1996).

Boykin D. et al., Anti–pneumocystis activity of bis–amidxímes and bis–o–alkylamidoximes prodrugs, *Biorganic and Medicinal Chemistry Letters*6, 3017–3020 (1996).

Weller T. et al. Orally active fibrinogen, *J. Med. Chem*39, 3139–3147 ( 1996).

Lopes, J.C.D. et al. Binding energy studies on the interaction between berenil derivatives and thrombin and the B–DNA dodecamer D(CGCGAATTCGCG)2, Chemical Abstracts 135, abstract No. 13816 (2001).

Rahmathullah et al. Prodrugs for amidines, *J. Med Chem*,42, 3994–4000 (1999).

* cited by examiner

PRODRUGS FOR ANTIMICROBIAL AMIDINES

CROSS-REFERENCE TO RELATED APPLICATIONS

The instant application claims priority to U.S. Provisional Application Ser. No. 60/142,826 filed Jul. 8, 1999, the disclosure of which is incorporated herein in its entirety.

The present invention was made with Government support under Grant Number 5-U19-AI33363 from the National Institutes of Health. The Government has certain rights to this invention.

FIELD OF THE INVENTION

The invention generally relates to methods for treating infections.

BACKGROUND OF THE INVENTION

A microbial infection such as, for example, *Pneumocystis carinii* pneumonia (PCP), is believed to be one of the leading causes of death in patients suffering from AIDS. Pentamidine [i.e., 1,5-bis(4-amidinophenoxy)pentane] has been used as a therapeutic agent for the treatment of PCP by intravenous infusion and as a prophylactic agent by aerosol dosage. However, the use of this drug may be potentially disadvantageous in that it might be toxic and contribute to hypotension, hypoglycemia, and cardiac arrhythmias experienced by the patient taking pentamidine.

Recent efforts have focused on developing other compounds for potentially treating PCP. A number of aromatic diamidines have displayed potential anti-PCP activity as reported in Boykin D. W., et al., *J. Med. Chem.*, 1995, pp. 912–916; Tidwell, R. R. et al., *Antimicrob. Agents Chemother.* 1993, 37, p. 1713; Lombardy, R. L. et al., *J. Med. Chem.* 1996, 39, p. 1452; and Kumar, A. et al., *J. Med. Chem.*, 1996, 31, p. 767. Notwithstanding any advantages that these drugs may possess, they may be potentially undesirable since the drugs often exhibit low oral bioavailability.

Chemical modification of drugs into prodrugs can potentially improve physiochemical properties such as water solubility, lipophilicity, transport of drug to the site of action, and presystemic degradation, thus improving oral bioavailability. See Bundgaard, H., In *Design of Prodrugs*; Bundgaard, H.;Ed.; Elsevier: Amsterdam, The Netherlands, 1985; pp. 1–92; and Bundgaard, H., In *A Textbook of Drug Design and Development*, Krogsgaard-Larsen, P.; Bundgaard, H.; Ed.; Harwood Academic Publ. Switzerland, 1991, pp. 113–191. A number of reports exist on the prodrug modification of carboxyl, hydroxyl, thiols, and amino compounds. See, for example, Friis, G. J., et al., In *A Textbook of Drug Design and Development*, $2^{nd}$ Ed., Krogsgaard-Larsen, P., Liljefors, T. Madsen, U.; Ed.; Overseas Pub: Amsterdam, The Netherlands, 1996, pp. 351–385; Digenis, G. A., et al., *Drug latentiation, Handbook of Experimental Pharmacology*, 1975, 28, pp. 86–112. Moreover, Weller et al. (*J. Med. Chem.*, 1996, 39, pp. 3139–3146) propose employing amidoximes and carbamate derivatives of monoamidines as prodrugs in order to potentially provide improved oral availability for fibrogen antagonists. In addition, Boykin, D. W., et al., (*Bioorg. Med. Chem. Lett.*, 1996, 6, pp. 3017–3020) have reported that bis-amidoxime and O-methylamidoxime may be effective anti-PCP agents on both oral and intravenous administration. U.S. Pat. No. 5,723,495 to Hall et al. proposes administering a bis-benzamidoxime to a patient for treating *Pneumocystis carinii*.

Notwithstanding the above efforts, there remains a need in the art to provide drugs that display improved activity.

SUMMARY OF THE INVENTION

A method of combating an infection to a subject in need of such a treatment is disclosed. The method comprises administering to the subject a compound of the formula (I):

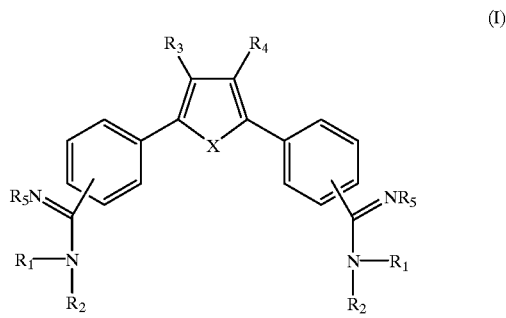

(I)

wherein:

X may be O, S, or NR' wherein R' is H or loweralkyl;

$R_1$ and $R_2$ may be independently selected from the group consisting of H, loweralkyl, oxyalkyl, alkoxyalkyl, cycloalkyl, aryl, hydroxyalkyl, aminoalkyl, and alkylaminoalkyl;

$R_3$ and $R_4$ are each independently selected from the group consisting of H, loweralkyl, halogen, oxyalkyl, oxyaryl, and oxyarylalkyl;

$R_5$ is represented by a formula selected from the group consisting of:

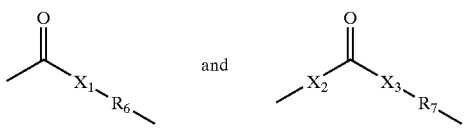

wherein:

$X_1$, $X_2$, and $X_3$ are independently selected from O and S; and $R_6$ and $R_7$ are independently selected from the group consisting of loweralkyl, aryl, alkylaryl, oxyaryl, an ester-containing substituent, and oxyalkyl;

or a pharmaceutically acceptable salt thereof, and wherein said compound of Formula (I) is administered in an amount to treat the infection.

Preferably, $R_6$ and $R_7$ are independently selected from the group consisting of:

$CH_3$, $CH_2CCl_3$, $CH_2CH_3$,

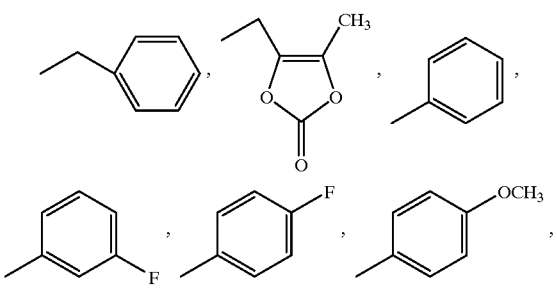

-continued
and

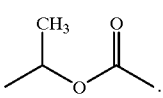

In one preferred embodiment, each of the substituents present on the compound of formula (I) represented by the formula:

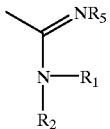

are present on the para positions of the aromatic groups on formula (I), although these substituents may be present in the meta positions.

The invention also discloses pharmaceutical compounds represented by the formula (I) described herein and pharmaceutically acceptable salts thereof, as well as pharmaceutical formulations comprising the pharmaceutical compounds of formula (I) and pharmaceutically acceptable carriers.

DETAILED DESCRIPTION OF THE PREFERRED EMBODIMENTS

Figure 1:
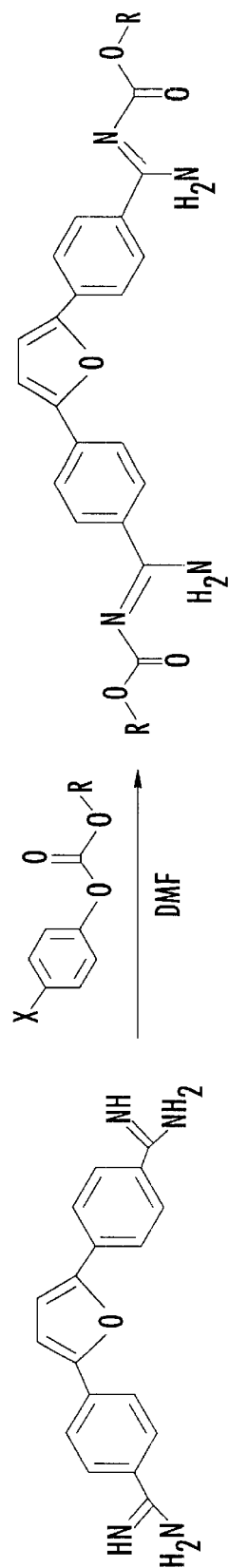
FIG. 1 illustrates a reaction in the synthesis of carbamates from 2,5-bis(4-amidinophenyl)furan.

The present invention now will be described more fully hereinafter with reference to the accompanying specification and examples, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

As used herein, the term "lower alkyl" refers to C1 to C4 linear or branched alkyl, such as methyl, ethyl, propyl, butyl, isopropyl, sec-butyl, and tert-butyl. The term "halogen" has its conventional meaning and refers to fluorine, chlorine, bromine, and iodine. The term "cycloalkyl" as used herein refers to C3 to C6 cyclic alkyl, such as cyclopropyl, cyclobutyl, cyclopentyl, and cyclohexyl. The term "aryl" as used herein refers to C3 to C10 cyclic aromatic groups such as phenyl, naphthyl, and the like, and includes substituted aryl groups such as, but not limited to, tolyl. The term "hydroxyalkyl" as used herein refers to C1 to C4 linear or branched hydroxy-substituted alkyl, i.e., —CH$_2$OH, —(CH$_2$)$_2$OH, etc. The term "aminoalkyl" as used herein refers to C1 to C4 linear or branched amino-substituted alkyl, wherein the term "amino" refers to the group NR'R", wherein R' and R" are independently selected from H or lower alkyl as defined above, i.e., —NH$_2$, —NHCH$_3$, —N(CH$_3$)$_2$, etc. The term "oxyalkyl" as used herein refers to C1 to C4 oxygen-substituted alkyl, i.e., —OCH$_3$, and the term "oxyaryl" as used herein refers to C3 to C10 oxygen-substituted cyclic aromatic groups. The term "alkoxyalkyl" as used herein refers to C1 to C4 linear or branched alkoxy, such as methoxy, ethoxy, propyloxy, butyloxy, isopropyloxy, and t-butyloxy. The term "ester-containing substitujent" refers to a substituent that may be directed linked to the compound of formula (I) via the single bond that is present directly off of the oxygen atom contained in the ester group or may be of the formula:

wherein R' and R" may be the same or different and can be substituted or unsubstituted alkyl that may be saturated or unsaturated. It should be appreciated that the various groups referred to above may be substituted or unsubstituted with various functional groups known to one skilled in the art.

As noted above, the methods of the present invention are useful for treating microbial infections such as *P. carinii* and *Giardia lamblia*. The compounds may also be useful in treating fungal infections such as *Candida albicans, Cryptococcus neoformans, Aspergillus fumigatus, Fusarium solani*, and combinations thereof. The methods of the invention are useful for treating these conditions in that they inhibit the onset, growth, or spread of the condition, cause regression of the condition, cure the condition, or otherwise improve the general well-being of a subject afflicted with, or at risk of contracting the condition.

Subjects to be treated by the methods of the present invention are typically human subjects, although the methods of the present invention may be useful with any suitable subject known to those skilled in the art.

As noted above, the present invention provides pharmaceutical formulations comprising the aforementioned active compounds, or pharmaceutically acceptable salts thereof, in pharmaceutically acceptable carriers for oral, intravenous, or aerosol administration as discussed in greater detail below. Also, the present invention provides such compounds or salts thereof which have been lyophilized and which may be reconstituted to form pharmaceutically acceptable formulations for administration, as by intravenous or intramuscular injection.

The therapeutically effective dosage of any specific compound, the use of which is in the scope of present invention, will vary somewhat from compound to compound, and patient to patient, and will depend upon the condition of the patient and the route of delivery. As a general proposition, a dosage from about 0.1 to about 50 mg/kg will have therapeutic efficacy, with all weights being calculated based upon the weight of the active compound, including the cases where a salt is employed. Toxicity concerns at the higher level may restrict intravenous dosages to a lower level such as up to about 10 mg/kg, with all weights being calculated based upon the weight of the active base, including the cases where a salt is employed. A dosage from about 10 mg/kg to about 50 mg/kg may be employed for oral administration. Typically, a dosage from about 0.5 mg/kg to 5 mg/kg may be employed for intramuscular injection. Preferred dosages are 1 μmol/kg to 50 μmol/kg, and more preferably 22 μmol/kg and 33 μmol/kg of the compound for intravenous or oral administration. The duration of the treatment is usually once per day for a period of two to three weeks or until the condition is essentially controlled. Lower doses given less frequently can be used prophylactically to prevent or reduce the incidence of recurrence of the infection.

In accordance with the present method, pharmaceutically active compounds as described herein, or pharmaceutically acceptable salts thereof, may be administered orally as a solid or as a liquid, or may be administered intramuscularly or intravenously as a solution, suspension, or emulsion. Alternatively, the compounds or salts may also be administered by inhalation, intravenously or intramuscularly as a liposomal suspension. When administered through inhalation the active compound or salt should be in the form of a plurality of solid particles or droplets having a particle size from about 0.5 to about 5 microns, and preferably from about 1 to about 2 microns.

The present invention also provides a pharmaceutical composition suitable for intravenous or intramuscular injection. The pharmaceutical composition comprises a compound of formula (I) described herein, or a pharmaceutically acceptable salt thereof, in any pharmaceutically acceptable carrier. If a solution is desired, water is the carrier of choice with respect to water-soluble compounds or salts. With respect to the water-insoluble compounds or salts, an organic vehicle, such as glycerol, propylene glycol, polyethylene glycol, or mixtures thereof, may be suitable. In the latter instance, the organic vehicle may contain a substantial amount of water. The solution in either instance may then be sterilized in a suitable manner known to those in the art, and typically by filtration through a 0.22 micron filter. Subsequent to sterilization, the solution may be dispensed into appropriate receptacles, such as depyrogenated glass vials. Of course, the dispensing is preferably be done by an aseptic method. Sterilized closures may then be placed on the vials and, if desired, the vial contents may be lyophilized.

In addition to compounds of formula (I) or their salts, the pharmaceutical compositions may contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the compositions may contain microbial preservatives. Useful microbial preservatives include methylparaben, propylparaben, and benzyl alcohol. The microbial preservative is typically employed when the formulation is placed in a vial designed for multidose use. Of course, as indicated, the pharmaceutical compositions of the present invention may be lyophilized using techniques well known in the art.

In yet another aspect of the present invention, there is provided an injectable, stable, sterile composition comprising a compound of Formula (I), or a salt thereof, in a unit dosage form in a sealed container. The compound or salt is provided in the form of a lyophilizate which is capable of being reconstituted with a suitable pharmaceutically acceptable carrier to form a liquid composition suitable for injection thereof into a subject. The unit dosage form typically comprises from about 10 mg to about 10 grams of the compound or salt. When the compound or salt is substantially water-insoluble, a sufficient amount of emulsifying agent which is physiologically acceptable may be employed in sufficient quantity to emulsify the compound or salt in an aqueous carrier. One such useful emulsifying agent is phosphatidyl choline.

Other pharmaceutical compositions may be prepared from the water-insoluble compounds disclosed herein, or salts thereof, such as aqueous base emulsions. In such an instance, the composition will contain a sufficient amount of pharmaceutically acceptable emulsifying agent to emulsify the desired amount of the compound or salt thereof. Particularly useful emulsifying agents include phosphatidyl cholines, and lecithin.

Further, the present invention provides liposomal formulations of the compounds disclosed herein and salts thereof. The technology for forming liposomal suspensions is well known in the art. When the compound or salt thereof is an aqueous-soluble salt, using conventional liposome technology, the same may be incorporated into lipid vesicles. In such an instance, due to the water solubility of the compound or salt, the compound or salt will be substantially entrained within the hydrophilic center or core of the liposomes. The lipid layer employed may be of any conventional composition and may either contain cholesterol or may be cholesterol-free. When the compound or salt of interest is water-insoluble, again employing conventional liposome formation technology, the salt may be substantially entrained within the hydrophobic lipid biayer which forms the structure of the liposome. In either instance, the liposomes which are produced may be reduced in size, as through the use of standard sonication and homogenization techniques.

Of course, the liposomal formulations containing the compounds disclosed herein or salts thereof, may be lyophilized to produce a lyophilizate which may be reconstituted with a pharmaceutically acceptable carrier, such as water, to regenerate a liposomal suspension.

Pharmaceutical formulations are also provided which are suitable for administration as an aerosol, by inhalation. These formulations comprise a solution or suspension of a desired compound described herein or a salt thereof, or a plurality of solid particles of the compound or salt. The desired formulation may be placed in a small chamber and nebulized. Nebulization may be accomplished by compressed air or by ultrasonic energy to form a plurality of liquid droplets or solid particles comprising the compounds or salts. The liquid droplets or solid particles should have a particle size in the range of about 0.5 to about 10 microns, more preferably from about 0.5 to about 5 microns. The solid particles can be obtained by processing the solid compound or a salt thereof, in any appropriate manner known in the art, such as by micronization. Most preferably, the size of the solid particles or droplets will be from about 1 to about 2 microns. In this respect, commercial nebulizers are available to achieve this purpose. The compounds may be administered via an aerosol suspension of respirable particles in a manner set forth in U.S. Pat. No. 5,628,984, the disclosure of which is incorporated herein by reference in its entirety.

Preferably, when the pharmaceutical formulation suitable for administration as an aerosol is in the form of a liquid, the formulation will comprise a water-soluble compound or a salt thereof, in a carrier which comprises water. A surfactant may be present which lowers the surface tension of the formulation sufficiently to result in the formation of droplets within the desired size range when subjected to nebulization.

As indicated, the present invention provides both water-soluble and water-insoluble compounds and salts thereof. As used in the present specification, the term "water-soluble" is meant to define any composition which is soluble in water in an amount of about 50 mg/mL, or greater. Also, as used in the present specification, the term "water-insoluble" is meant to define any composition which has solubility in water of less than about 20 mg/mL. For certain applications, water soluble compounds or salts may be desirable whereas for other applications water-insoluble compounds or salts likewise may be desirable.

In another aspect, the invention relates to a process for making a pharmaceutically active bis-aryl carbamate represented by formula (I). The process comprises reacting an aryl carbonate with bis-amidine in the presence of an organic solvent to form the bis-aryl carbamate.

In one embodiment, the aryl carbonate may be represented by the formula:

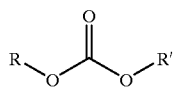

wherein:
R is represented by:

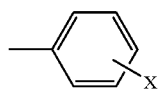

wherein X is selected from the group consisting of H, $NO_2$, F, and $OCH_3$; and wherein R' is selected from the group consisting of $CH_3$, $CH_3CH_2$, $CH_2CCl_3$, $CH(OAc)CH_2$, $CH_2C_6H_5$, and

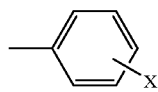

wherein X is selected from the group consisting of H, $NO_2$, F, and $OCH_3$. The aryl carbonate may be a symmetrical aryl carbonate. Specific examples of aryl carbonates include, but are not limited to, diphenyl carbonate, bis(4-fluorophenyl)carbonate, bis(4-methoxyphenyl)carbonate, benzyl-4-nitrophenylcarbonate, 4-nitrophenyl thioethyl carbonate, and 4-nitrophenyl-2,2,2-trichloroethyl carbonate, methyl 4-nitrophenyl carbonate, bis (3-fluorophenyl) carbonate, ethyl 4-nitrophenyl carbonate, (4-methyl-2-oxo-1,3-dioxol-4-en-5-yl) methyl 4-nitrophenyl carbonate, and 1-acetoxyethyl 4-nitrophenyl carbonate.

Examples of the pharmaceutically active bis-aryl carbamate that may be formed by the process of the invention include, but are not limited to, 2,5-bis[4-(N-2,2,2-trichloroethoxycarbonyl)amidinophenyl]furan, 2,5-bis[4-(N-thioethylcarbonyl)amidinophenyl]furan, 2,5-bis[4-(N-benzyloxycarbonyl)amidinophenyl]furan, 2,5-bis[4-(N-phenoxycarbonyl)amidinophenyl]furan, 2,5-bis[4-(N-(4-fluoro)phenoxycarbonyl)amidinophenyl]furan, 2,5-bis[4-(N-(4-methoxy)phenoxycarbonyl)amidinophenyl]furan, 2,5-bis[4(1-acetoxyethoxycarbonyl)amidinophenyl]furan, and 2,5-bis[4-(N-(3-fluoro)phenoxycarbonyl) amidinophenyl]furan.

Preferred organic solvents that may be employed in the process of the invention include, but are not limited to, dimethyl formamide, tetrahydrofuran/$CH_3CN$, and dioxane. Typically, tetrahydrofuran/$CH_3CN$ is employed in the presence of a base such as, but not limited to, diisopropylethylamine and triethylamine.

In addition to the above, the compounds described herein may be formed by various methods such as, for example, those described in Weller, T., et al., *J. Med. Chem.* 1996, 39, 3139–3146. Such a method typically relates to preparing a carbamate from amines of amidines involving the reaction of the base with an appropriate chloroformate in the presence of a base, typically aqueous sodium hydroxide or sodium/potassium bicarbonate. Nonetheless, since this method may suffer from potential drawbacks, an alternative method is disclosed herein for preparing carbamates from amidines by reaction with carbonates, and in particular aryl-alkyl and aryl-aryl carbonates. Traditionally carbonates have been prepared by the reaction of tertiary amines and chloroformates. See Olofson, R. A., et al., *J. Org. Chem.* 1984, 49, pp. 2081–2082; and Olofson, R. A. *Pure and Appl. Chem.* 1988, 60, pp. 1715–1724. Additionally, the dealkylation of tertiary aliphatic amines with phenyl chlorothionoformate has been reported in Millan D. S., et al., *Tetrahedron Lett.* 1998, 39, pp. 4387–4390.

A method for preparing carbonates is disclosed herein in which pyridine is used as a base. As an example of the method, the 4-nitrophenylalkyl carbonates described herein were prepared by reacting 4-nitrophenol with the corresponding alkyl or arylchloroformates in methylene chloride ($CH_2Cl_2$) using pyridine as a base. (1-acetyloxy)ethyl-4-nitrophenyl carbonate was prepared from 1-chloroethyl-4-nitrophenyl carbonate according to published procedures. See Alexander, J. et al., *J. Med. Chem.*, 1991, 34, pp. 78–81; and Lin, Y. I., et al., *Bioorg. Med. Chem. Lett.*, 1997, 7, pp. 1811–1816. Symmetrical carbonates (i.e., diphenyl and bis (4-fluoro)- and bis(4-methoxy)phenylcarbonates described as 20–22) were synthesized by reacting phenol, 4-fluorophenol, and 4-methoxyphenol with phenyl, 4-fluorophenyl, and 4-methoxypehnyl chloroformates respectively in a pyridine/$CH_2Cl_2$ medium. 4-nitrophenyl (5-methyl-2-oxo-1,3-dioxo-4-ene-1-yl) methyl carbonate (23) was synthesized from commercially available 4,5-dimethyl-1,3-dioxol-2-one by a four-step process as outlined in Sakamoto, F. et al., *Chem. Pharm. Bull.*, 1984, 32, pp. 2241–2248. A modification to this procedure has been proposed in the bromination step which ultimately leads to the carbonate 23. The bromination of dimethyl dioxolone with N-bromosuccinimide in carbon tetrachloride in the presence of α,α-azoisobutyronitrile as a free radical initiator under reflux conditions for 16 hours can afford the monobromide as a major product (90 percent) and dibromide as a minor product (10 percent). Displacement of the bromide by formate followed by acid catalyzed hydrolysis to give hydroxymethyl derivative was carried out according to a modification of a procedure described in Alpegiani, M. et al., *Synth. Commun.*, 1992, 22, pp. 1277–1282.

The synthesis of carbamates from amines is well known. The invention provides for the synthesis of carbamates of aromatic amidines. Methyl carbamate 2 was synthesized by the known method of reacting bis-amidine 1 with methylchloroformate in $CH_2Cl_2$ employing sodium hydroxide as a base, often obtaining yields less than 50 percent. An alternative approach to potentially improve the yield and purity of the carbamate involves reacting bis-amidine 1 with methyl-4-nitrophenyl carbonate in DMF to obtain methyl carbamate 2 at a yield of 80 percent. Carbamates 3–10 set forth in Table 1 were synthesized from bis-amidine 1 and the appropriate carbonates in DMF or THF/$CH_3CN$ (see Scheme 1). A base was not employed when using DMF. A base (e.g., diisopropylethylamine) was used when employing THF/$CH_3CN$. Symmetrical carbonates were reacted with bis-amidine 1 to obtain the expected carbamates (7–9).

Table 1 contains the results of evaluation of the carbamate and carbamate prodrugs 2–11 against *P. carinii* pneumonia in an immunosuppressed rat model (see S. K. Jones et al., *Antimicrob. Agents Chemother.* 1990, 34, pp. 1026–1030). Most of the prodrugs 2–11 appear to be metabolized in vivo and were generally effective against PCP, orally and intraveneously.

EXAMPLES

The invention will now be described in greater detail with reference to the following examples. It should be noted that these examples are for illustrative purposes only, and are not meant to limit the invention.

Examples 1–25

Experimental Procedure

In the examples which follow, melting points were recorded using a Thomas-Hoover (Uni-Melt) capillary melting point apparatus and were uncorrected. TLC analysis was carried out on silica gel 60 $F_{254}$ pre-coated aluminum sheets (0.20 mm layer thickness) (E. Merck of Whitehouse Station, N.J.) and detected under UV light. IR spectra were recorded using Perkin-Elmer Model 337 spectrometer sold by Perkin-Elmer of Norwalk, Conn. $^1$H and $^{13}$C NMR spectra were recorded employing a Varian GX400 or a Varian Unityplus 300 spectrometer (both sold by Varian of Palo Alto, Calif.) and chemical shifts (δ) are in ppm relative to TMS as internal standard. Mass Spectra were recorded on a VG Analytical 70-SE spectrometer (Georgia Institute of Technology, Atlanta, Ga.). IR spectra were recorded using a Perkin-Elmer 2000 instrument. Elemental analyses were obtained from Atlantic Microlab Inc. of Norcross, Ga. and are believed to be within 0.4 percent of the theoretical values unless otherwise mentioned. All chloroformates were purchased from Aldrich Chemical Co. of St. Louis, Mo. Other chemicals and solvents were purchased from either Aldrich or Fischer Scientific of Houston, Tex. 4,5-Dimethyl-1,3-dioxol-2-one was purchased from TCI America Inc. 2,5-Bis(4-cyanophenyl)furan, 2,5-bis(4-amidinophenyl)furan, and 2,5-bis[4-(N-hydroxy)amidinophenyl]furan were synthesized as previously described. See Baijic, M., et al., *Heterocycl. Commun.*, 1996, 2, pp.135–140; Das, B. P., *J. Med. Chem.* 1977, 20, pp. 531–536; and Boykin, D. W., et al., *Bioorg. Med. Chem Lett.*, 1996, 6, pp. 3017–3020. Anti-*Pneumocystis carinii* pneumonia activity screening was carried out according to published methods. See Jones, S. K. et al., *Antimicrob. Agents Chemother.*, 1990, 34, pp.1026–1030; Hall, J. E., et al., *Antimicrob. Agents Chemother.*, 1998, 42, pp. 666–674; and Tidwell, R. R., et al., *J. Med. Chem.*, 1990, 33, pp. 1252–1257. Compounds were routinely tested orally at 33 μmol/kg/day and intravenously at 22 μmol/kg/day. Saline and pentamidine treated groups of rats were included as negative and positive controls, respectively.

Bold numbers that are listed in connection with each example correspond to the numbers listed in Table 1.

Example 1

Synthesis of Methyl 4-nitrophenyl carbonate (12)

To an ice cold solution of 4-nitrophenol (7.36 g, 0.053 mol) and pyridine (4.3 g, 0.054 mol) in $CH_2Cl_2$ (80 mL) at 0–5° C. was added a solution of methylchloroformate(5 g, 0.053 mol) in $CH_2Cl_2$ (20 mL) and stirred for 15 min and then at room temperature overnight (16 h). The mixture was extracted with $CH_2Cl_2$ (50 mL), washed successively with water (50 mL), aq. NaOH (0.5 N, 50 mL), sat. aq. NaCl solution (50 mL), water (3 –50 mL) and dried ($Na_2SO_4$). The $CH_2Cl_2$ solution was passed through a silicagel column using chloroform (100%) as eluent to furnish pure carbonate 12 (10 g, 96%) as a white solid. Purification of the carbonate by recrystallization gave 80% yield: TLC ($R_f$) 0.50 (100% $CHCl_3$); mp 111–112° C.; IR (KBr) 3121, 3086, 1766, 1618, 1602, 1522, 1443, 1366, 938, 858, 667 cm$^{-1}$; $^1$H NMR ($CDCl_3$) 8.24 (d, 2H, J=9.05 Hz, Ar—CH), 7.34 (d, 2H, J=9.05 Hz, Ar—CH), 3.91 (s, 3H, $OCH_3$); $^{13}$C NMR ($CDCl_3$), 155.71 (OCOO), 153.28 (Ar—OCO), 145.61 (C—$NO_2$), 125.51 (Ar—CH), 121.96 (Ar—CH),56.07 ($OCH_3$); MS m/e (El$^+$, relative intensity, %) 197 (25), 153 (33), 123 (100), 95 (21), 92 (45), 77 (46), 64 (32), 63 (33), 59 (55).

Example 2

2,5-Bis[4-(N-methoxycarbonyl)amidinophenyl]furan (2)

To a stirring suspension of bis-amidine 1 (0.5 g, 0.00164 mol) in dry DMF (8 mL) at room temperature, was added a solution of methyl 4-nitrophenyl carbonate (0.72 g, 0.0036 mol) in DMF (2mL) and the mixture was stirred overnight (16 h). Water (20 mL) was added to the mixture, stirred for few min and filtered, washed with water (2×10 mL), and ether (10 mL) and dried. Crystallization from ethanol gave pure carbamate 2 (80%) as a white solid: TLC ($R_f$) 0.49 ($CHCl_3$, MeOH, $NH_4OH$, 4:1:0.2, v/v); mp >300° C. dec.; IR (KBr) 3500–3100, 3010, 2956, 1672, 1609, 1566, 1518, 1476, 1442, 1266, 1198, 1147, 1124, 1086, 1030, 940, 856, 806, 786, 764, 674, 604, 548 cm$^{-1}$; $^1$H NMR (DMSO-$d_6$) δ 9.11 (s, 4H, NH), 8.07 (d, 2H, J=8.18 Hz, Ar—CH), 7.95 (d, 2H, J=8.30 Hz, Ar—CH), 7.30 (s, 2H, furan-CH), 3.63 (s, $NCOOCH_3$); $^{13}$C NMR (DMSO-$d_6$) δ 165.61, 164.36, 152.61, 132.96, 132.81, 128.36, 123.34, 110.52, 51.85 MS m/z (FAB, thioglycerol) 421 (M+1), 389, 363, 346, 321, 305, 289, 271, 257, 237, 230. Anal. ($C_{22}H_{20}N_4O_5$) C,H,N.

Example 3

Synthesis of 4-nitrophenyl-2,2,2-trichloroethyl carbonate (14)

To an ice cold solution of 4-nitrophenol (2.0 g, 14.4 mmol) and triethylamine (1.6 g, 15.8 mmol) (or pyridine) in $CH_2Cl_2$ (20 mL) at 0–5° C. was added a solution of 2,2,2-trichloroethylchloroformate (3.2 g, 15 mmol) in $CH_2Cl_2$ (10 mL) and stirred for 15 min. and then at room temperature overnight (16 h). Aqueous work up as described above and purification of the product by silicagel column chromatography using chloroform (100%) as eluent furnished pure carbonate 14 (4.3 g 91%). Alternatively, the product is purified by recrystallization from hexane in 60% yield: TLC ($R_f$) 0.56 (100% $CHCl_3$); mp 59–60° C.; IR (KBr) 3123, 3093, 3012, 2967, 2871, 2462, 2365, 2343, 1771, 1630, 1541, 1496, 1432, 1362, 1288, 1251, 1020, 954, 843, 783 cm$^{-1}$; $^1$H NMR ($CDCl_3$) δ 8.33 (d, 2H, J=9.36 Hz, Ar—CH), 7.45 (d, 2H, J=9.36 Hz, Ar—CH), 4.91 (s, 2H, $OCH_2CCl_3$), $^{13}$C NMR ($CDCl_3$) δ 155.21 (OCOO), 151.68 (Ar—OCO), 145.91 (C—$NO_2$), 125.64, 121.89, 93.95 ($CCl_3$), 77.56 ($CH_2CCl_3$); MS m/e (El$^+$, relative intensity, %) 314 (M$^+$, 1), 313 (5), 280 (17), 278 (26), 196 (14), 182 (25), 166 (74), 139 (100), 135 (20), 133 (57), 131 (58), 122 (24), 109 (40), 95 (32), 63 (22). Anal. ($C_9H_6NO_5Cl_3$) C,H.

Example 4

Synthesis of 2,5-bis[4-(N-2,2,2-trichloroethoxycarbonyl)amidinophenyl]furan (3)

To a suspension of amidine 1 (0.5 g, 0.00164 mol) and diisopropylethylamine (0.43 g, 0.0033 mol) in THF/$CH_3CN$ mixture (20 mL, 1:1 v/v) at room temperature, was added a solution of 4-nitrophenyl-2,2,2-trichloroethyl carbonate (1.1 g, 0.0035 mol) in THF (10 mL) and stirred for 24 h. The solvents were removed in a rotavapor and the residue was cooled in ice, triturated with anhydrous diethyl ether (20 mL), filtered, washed with ether (2×20 mL), dried and crystallized from $CHCl_3$-ether mixture to obtain 2,2,2-trichloroethylcarbamate (3) (0.65 g, 60% yield) as a yellow solid: TLC ($R_f$) 0.6; ($CHCl_3$, MeOH, $NH_4OH$, 4:1:0.2, v/v); mp 134–136° C.; IR (KBr) 3509–3029, 3010, 2997, 2952, 1682, 1615, 1600, 1517, 1492, 1485, 1412, 1377, 1251, 1147, 1130, 1120, 1058, 1028, 939, 849, 798, 730, 716, 634, 560 $cm^{-}$; $^1H$ NMR (DMSO-$d_6$) δ 9.80–9.60 (br s, 4H, NH), 8.07 (d, J=8.73 Hz, 4H, Ar—CH), 8.02 (d, J=8.73 Hz, 4H, Ar—CH), 7.39 (s, 2H, CH-furan), 4.98 (s, 4H, $OCH_2CCl_3$); $^{13}C$ NMR (DMSO-$d_6$) δ 166.35, 152.58, 133.57, 129.23, 123.39, 111.23, 95.57 ($CCl_3$), 74.49 ($CH_2CCl_3$); MS m/z (FAB, thioglycerol): 656 (M+1, 9 isotopic peaks), 507 (7 peaks), 481 (8 peaks), 481 (8 peaks), 464.0 (6 peaks), 357 (3 peaks), 314 (3 peaks), 304, 288, 271, 262, 245, 232. Anal. ($C_{24}H_{18}N_4O_5Cl_6$) C, H, N.

Example 5

Synthesis of 4-nitrophenyl thioethyl carbonate (18)

Thiocarbonate 18 was synthesized from 4-nitrophenol and thioethylchloroformate in pyridine/$CH_2Cl_2$ as described previously, in 92% yield and subsequently purified by silica column chromatography to afford pure colorless crystals: TLC ($R_f$) 0.6 (100% $CHCl_3$); mp 65–66° C.; IR (KBr) 3120, 3089, 2944, 2588, 2000, 1942, 1740, 1528, 1454, 1352, 1198, 1102, 894, 748, 660, 526 $cm^{-}$; $^1H$ NMR ($CDCl_3$) d 8.25 (dd, 2H, J=4.92, 2.07 Hz, Ar—CH), 7.33 (dd, 2H, J=4.92, 2.22 Hz, Ar—CH), 2.96 (q, 2H, J=14.84 Hz, $SCH_2$), 1.38 (t, 3H, J=7.46 Hz, $CH_3$); $^{13}C$ NMR ($CDCl_3$) d 169.70, 155.79, 145.52, 125.44, 122.21, 26.04 ($SCH_2$), 14.85 ($CH_3$); MS m/e (El$^+$, relative intensity, %) 227 (M$^+$, 4), 139 (12), 109 (19), 89 (100), 63 (12). Anal. ($C_9H_9NO_4S$) C,H.

Example 6

Synthesis of 2,5-bis[4-(N-thioethylcarbonyl) amidinophenyl]furan(4)

To a suspension of bis-amidine 1 (0.6 g, 0.002 mol) in DMF (10 mL) at room temperature, was added a solution of 4-nitrophenyl ethylthiocarbonate (0.9 g, 0.004 mol). The resulting solution was stirred for 24 h. Ice water (40 mL) was added to the mixture and filtered, washed with water (3×30 mL), ether (30 mL) and dried. The crude solid was purified by crystallization from ethanol-ether to furnish carbamate 4 (0.6 g, 62%) as a yellow solid: TLC ($R_f$) 0.58 ($CHCl_3$, MeOH, $NH_4OH$, 4:1:0.2, v/v); mp >300°; IR (KBr) 3442–3200, 3040, 2970, 2928, 2866, 1668, 1610, 1592, 1562, 1469, 1413, 1382, 1320, 1305, 1283, 1208, 1130, 1110, 1090, 1016, 939, 885, 842, 768 $cm^{-1}$; $^1H$ NMR (DMSO-$d_6$) δ 9.26 (d, 4H, $D_2O$ exchangeable, J=45 Hz, NH), 8.07 (d, 4H, J=8.42 Hz, Ar—CH), 7.96 (d, 4H, J=8.30 Hz, Ar—CH), 7.31 (s, 2H, CH-furan), 2.78 (q, 4H, J=14.3 Hz, $SCH_2$), 1.24 (t, 6H, J=7.32 Hz, $SCH_2CH_3$); $^{13}C$ NMR (DMSO-$d_6$) δ 181.37, 162.06, 152.64, 132.95, 132.35, 128.70, 123.43, 110.76, 24.06 ($SCH_2$), 15.34 ($SCH_2CH_3$); MS m/z (FAB, m-nitrobenzoic acid) 481 (M+1), 429, 413, 397, 321, 298, 272, 257, 231. Anal. ($C_{24}H_{24}N_4O_3S_2 \cdot 0.25H_2O$) C, H, N.

Example 7

Benzyl-4-nitrophenylcarbonate (19)

Carbonate 19 was synthesized from 4-nitrophenol and benzylchloroformate as described above, in 80% yield after silica column purification, as a white solid: TLC ($R_f$) 0.55 (100% $CHCl_3$); mp 81° C.; IR (KBr) 3098, 3034, 2855, 1758, 1617, 1528, 1387, 1355, 1285, 1227, 1112, 1049, 965, 870, 780, 729, 583, 511 $cm^{-1}$; $^1H$ NMR ($CDCl_3$) d 8.26 (d, 2H, J=9.4 Hz), 7.43 (m, 5H, Ar—CH of benzyl), 7.37 (d, 2H, J=9.4 Hz, $OCH_2$—Ar); $^{13}C$ NMR ($CDCl_3$): δ 155.53, 152.45, 145.40, 134.20, 129.07, 128.81, 128.66, 125.30, 121.77, 71.01; MS m/e (El$^+$, relative intensity, %) 274, 244, 230, 199, 140, 131, 108.

Example 8

Synthesis of 2,5-bis[4-(N-benzyloxycarbonyl) amidinophenyl]furan (5) and dimaleate Salt To a suspension of bis-amidine 1 (0.5 g, 0.0016 mol) in DMF (10 mL) at room temperature, was added benzyl-4-nitrophenylcarbonate (1.6 g, 0.006 mol). The resulting solution was stirred for 24 h and ice water (40 mL) was then added and extracted with $CHCl_3$ (2×50 mL). The $CHCl_3$ extract was washed with aq. NaOH (1 N, 40 mL), sat. NaCl (40 mL), water (50 mL) and dried ($Na_2SO_4$). The solution was filtered, concentrated in a rotavapor, cooled in ice bath, triturated with ether (30 mL), filtered, washed with ether (3×20 mL) and dried under vacuum for 16 h to afford carbamate 5 as a shiny pale yellow solid (0.77 g, 52%): TLC ($R_f$) 0.76 ($CHCl_3$, MeOH, $NH_4OH$, 4:1:0.2, v/v); mp 225° C. dec.; IR (KBr) 3480–3140, 3111, 3087, 3063, 3032, 2960, 2866, 1667, 1612, 1570, 1507, 1497, 1375, 1296, 1266, 1145, 926, 859, 787, 744, 702 $cm^{-1}$; $^1H$ NMR (DMSO-$d_6$) δ 9.16 (s, 4H, $D_2O$ exchangeable, NH), 8.09 (d, 4H, J=8.57 Hz, Ar—CH), 7.95 (d, 4H, J=8.57 Hz, Ar—CH), 7.42–7.31 (2×d+3×t, 10H, Ar—CH), 7.30 (s, 2H, CH-furan), 5.13 (s, $OCH_2Ph$, 4H $^{13}C$ NMR (DMSO-$d_6$) δ165.97, 163.69, 152.62, 137.12, 132.89, 132.86, 128.44, 128.35, 127.97, 127.77, 123.35, 110.60, 66.04 ($OCH_2Ph$); MS m/e (FAB, m-nitrobenzoic acid) 573 (M+1), 460, 439, 421, 378. Anal. ($C_{34}H_{28}N_4O_5 \cdot 2H_2O$) C, H, N.

A mixture of the carbamate free base 5 (0.4 g, 0.0007 mol), maleic acid (0.18 g, 0.0016 mol) and dry ethanol (20 mL) was stirred at room temperature for 4 h. The mixture was cooled in ice bath, triturated with dry $Et_2O$ (25 mL), filtered, washed with $Et_2O$ (3×10 mL) and dried in a vacuum oven at 50° C. overnight to afford 5-dimaleate salt as a yellow solid (0.53 g, 94%): mp 155–157° C. dec.; IR (KBr); 3480–3140, 3111, 3087, 3063, 3032, 2960, 1667, 1612, 1570, 1507, 1497, 1375, 1266, 1145, 926, 859, 787, 744, 702 $cm^{-1}$; $^1H$ NMR (DMSO-$d_6$) δ9.40–9.80 (br s, 2H, $D_2O$ exchangeable, NH), 8.03 (d, 4H, J=8.56 Hz, Ar—CH), 7.99 (d, 4H, J=8.56 Hz, Ar—CH), 7.42–7.31 (2×d+3×t, 10H, Ar—CH), 7.35 (s, 2H, CH-furan), 6.18 (s, 2H, $O_2CCH=CHCO_2$), 4.19 (s, 4H, $OCH_2Ph$); $^{13}C$ NMR (DMSO-$d_6$) δ 166.77, 165.49, 152.57, 136.39, 133.34, 132.07, 128.94, 128.39, 128.11, 128.01, 123.36, 111.03, 66.72 ($OCH_2Ph$); MS m/e (FAB, m-nitrobenzoic acid) (free base) 573.2, 460.1, 421.2, 378.2; Anal. ($C_{42}H_{36}N_4O_{13}$) C, H, N.

Example 9

Synthesis of 4-bromomethyl-5-methyl-1,3-dioxol-2-one

A mixture of 4,5-dimethyl-1,3-dioxol-2-one (15.0 g, 0.132 mol), a,a-azobisisobutyronitrile (AIBN) (1.08 g, 0.0066 mol) and N-bromosuccinimide (23.4 g, 0.132 mol) in freshly distilled carbon tetrachloride (350 mL) was refluxed under nitrogen for 16 h. The mixture was concentrated to one-half the initial volume, cooled in an ice bath and the white solid was filtered off. Concentration of the filtrate (CCl$_4$ solution) in a rotavapor under reduced pressure gave 4-bromomethyl-5-methyl-1,3-dioxol-2-one as a pale brown liquid in 90% yield (25 g). Due to the instability of the product at room temperature, it was used without purification for the next step. However, a small amount of the crude produce (100 mg) was purified for NMR analysis, through a short pad of silicagel using CHCl$_3$ (100%) as eluent. $^1$H NMR (CDCl$_3$) δ4.21 (s, 2H, CH$_2$Br), 2.14 (s, 3H, CH$_3$); $^{13}$C NMR (CDCl$_3$) δ 151.72 (OCOO, 138.08 (=CCH$_2$Br), 134.62 (=C—CH$_3$), 18.01 (CH$_2$Br), 9.51 (CH$_3$).

Example 10

Synthesis of (5-methyl-1,3-dioxol-2-one-4-yl) methyl formate

To an ice cold solution of 4-bromomethyl-5-methyl-1,3-dioxol-2-one (24 g, 0.124 mol) and formic acid (19.5 g, 0.43 mol) in acetonitrile (250 mL) at 0° C. was added triethylamine (44 g, 0.44 mol) dropwise over a period of 15 min. Ice bath was then removed and the mixture was stirred at room temperature for 2 h. The mixture was concentrated to one-half the initial volume on a rotavapor and extracted with ethyl acetate (2×150 mL). The organic extract was washed successively with satd. NaHCO$_3$ (200 mL), said. NaCl (200 mL), water (200 mL) and dried (Na$_2$SO$_4$). Concentration of the filtrate gave crude formate ester as a colorless liquid (20 g): $^1$H NMR (CDCl$_3$) δ 8.06 (s, 1H, CH$_2$OOCH), 4.91 (s, 2H, CH$_2$), 2.16 (s, CH$_3$); $^{13}$C NMR (CDCl$_3$) δ 160.26 (CH$_2$OOCH), 152.06 (OCOO), 140.59 (=CCH$_2$), 133.14 (=C—CH$_3$), 53.15 (CH$_2$OOCH), 9.42 (CH$_3$).

Example 11

Synthesis of 4-Hydroxymethyl-5-methyl-1,3-dioxol-2-one

To a solution of the crude formate (19.9 g) and 80% methanol (250 mL) at room temperature was added conc. HCl (1 mL) and stirred for 6 h. Methanol was evaporated off in rotavapor at 30° C. under reduced pressure and the residue was extracted with ethyl acetate. Passage through a short pad of silica gel and concentration gave 4-hydroxymethyl-5-methyl-1,3-dioxol-2-one as a colorless oil (7.0 g, 43%): $^1$H NMR (CDCl$_3$) δ 4.37 (s, 2H, CH$_2$OH), 2.80 (s, 1H, OH, D$_2$O exchangeable), 2.11 (s, 3H, CH$_3$); $^{13}$C NMR (CDCl$_3$) δ 152.94 (OCOO), 137.63 (=CCH2OH), 135.01 (=CCH$_3$), 53.32 (CH$_2$OH), 9.33 (CH$_3$).

Example 12

Synthesis of 4-methyl-2-oxo-1,3-dioxiol-4-en-5-yl) methyl-4-nitrophenyl carbonate (23)

Carbonate 23 was synthesized from 4-methyl-5-hydroxymethyl-1,3-dioxol-4-ene-2-one and 4-nitrophenylchloroformate in CH$_2$Cl$_2$/pyridine and purified by crystallization from chloroform colorless crystals in 76% yield: TLC (R$_f$) 0.23 (100% CHCl$_3$); mp 120–121° C. (lit.$^{31}$ 116–117° C); IR (KBr) 3115, 3096, 2928, 2854, 1811, 1780, 1742, 1619, 1593, 1525, 1494, 1352, 1308, 1246, 1221, 1054, 860, 768 cm$^{-1}$; $^1$H NMR (CDCl$_3$) δ 8.29 (d, 2H, J=9.04 Hz), 7.39 (d, 2H, J=9.20 Hz), 5.03 (s, 3H, C=CCH$_3$), 2.22 (s, 2H, OCOOCH$_2$); $^{13}$C NMR (CDCl$_3$) δ 155.36 (OC=OO), 152.46, 151.85 (vinylene C=O), 145.93 (Ar—NO$_2$), 141.62, 132.45, 125.59, 121.90, 58.37 (OCH$_2$), 9.65 (C=CCH$_3$); MS m/e (El$^+$, relative intensity, %) 295 (M$^+$, 1), 139 (9), 113 (100), 69 (23), 43 (74). Anal. (C$_{12}$H$_9$NO$_8$) C, H, N.

Example 13

Synthesis of 2,5-bis{4-[N-(5-methyl-2-oxo-1,3-dioxol-4-ene-1-yl)methoxycarbonyl] amidinophenyl}furan (6)

To a suspension of bis-amidine 1 (0.7 g, 0.0023 mol) in DMF (15 mL) at room temperature, was added a solution of (4-methyl-2-oxo-1,3-dioxol-4-ene-1-yl) methyl 4-nitrophenyl carbonate (1.5 g, 0.0052 mol) in DMF (5 mL) and stirred for 24 h. Ice water (50 mL) was added, filtered, washed with water (3×20 mL), ether (30 mL) and dried under vacuum. The crude product was crystallized from CHCl$_3$-ether mixture to yield pure 6 (1.26 g. 89%) as a yellow solid: TLC (R$_f$) 0.33 (CHCl$_3$, MeOH, NH$_4$OH, 4:1:0.2, v/v); mp 153–155° C.; IR (KBr) 3500–3120, 3105, 3075, 2866, 3037, 1825, 1667, 1660, 1618, 1610, 1521, 1497, 1417, 1394, 1266, 1230, 1145, 1094, 989, 927, 787, 687 cm$^{-1}$; $^1$H NMR (DMSO-d$_6$) δ 9.19 (s, 4H, D$_2$O exchangeable, NH), 8.09 (d, J=8.43 Hz, Ar—CH), 7.96 (d, 4H, J=8.24 Hz, Ar—CH), 7.31 (s, 2H, CH-furan), 4.95 (s, 4H, OCH$_2$), 2.18 (s, 6H, C=CCH$_3$); $^{13}$C NMR (DMSO-d$_6$) δ 166.23, 162.91, 152.60 (C=O, dioxolone), 151.96, 139.53, 134.09, 132.96, 132.65, 128.47, 123.35, 110.66, 54.17 (OCH$_2$), 8.82 (C=CCH$_3$); MS m/z (FAB, m-nitrobenzoic acid) 617 (M+1), 505, 487, 460, 443, 424, 375, 357. Anal. (C$_{36}$H$_{24}$N$_4$O$_{11}$) C, H, N.

Example 14

Synthesis of diphenyl carbonate (20)

Carbonate 20 was prepared by reaction of phenol with phenylchloroformate in pyridine/CH$_2$Cl$_2$ followed by aqueous workup as described above in 90% yield as a white solid: TLC (R$_f$) 0.7 (100% CHCl$_3$); mp 79–80° C.; IR (KBr) 3066, 1776, 1604, 1495, 1457, 1400, 1285, 1189, 997, 755, 691 cm$^{-1}$; $^1$H NMR (CDCl$_3$) δ 7.40 (t, 4H, J=8.02 Hz), 7.26 (d, 6H, J=8.73 Hz); $^{13}$C NMR (CDCl$_3$) δ 152.29, 151.14, 129.77, 126.50, 121.10; MS m/e (El$^+$, relative intensity, %) 214 (M$^+$, 100), 170 (46), 169 (37), 142 (43), 141 (64), 94 (13), 77 (87), 65 (26), 51 (25), 39 (23).

Example 15

Synthesis of 2,5-Bis[4-(N-phenoxycarbonyl) amidinophenyl]furan (7)

To a suspension of bis-amidine 1 (0.5 g, 0.0016 mol) in DMF (10 mL) at room temperature, was added diphenylcarbonate (0.77 g, 0.0036 mol). The resulting solution was stirred for 24 h and ice water (40 mL) was then added and the resulting solid was filtered, washed with plenty of water (3×30 mL), ether (2×30 mL) and dried under vacuum in a dessicator for 16 h to furnish carbamate 7 (0.53 g, 63%) as a yellow solid: TLC (R$_f$) 0.68 (CHCl$_3$, MeOH, NH$_4$OH, 4:1:0.2, v/v); mp>300° C.; IR (KBr) 3680–3000, 1674, 1615, 1462, 1515, 1488, 1412, 1382, 1266, 1199, 1170, 1145, 1030, 1016, 939, 969, 864, 798, 738, 693, 589 cm$^{-1}$; $^1$H NMR (DMSO-d$_6$) δ 9.30 (s, 4H, D$_2$O exchangeable, NH), 8.12 (d, 4H, J=7.61 Hz, Ar—CH), 7.98 (d, 4H, J=7.30 Hz, Ar—CH), 7.44 (t, 4H, J=7.46 Hz, Ar-m-H), 7.33 (s, 2H, CH-furan), 7.22 (t, 2H, J=6.19 Hz, Ar-p-CH), 7.20 (d, 4H, J=8.57 Hz, Ar-o-CH); $^{13}$C NMR (DMSO-d$_6$) δ 166.78, 162.12, 152.65, 151.63, 151.63, 133.08, 132.58, δ 129.17, 128.59, 124.92, 123.43, 121.95, 115.19, 110.79; MS m/z (FAB, m-nitrobenzoic acid) 545 (M+1), 460, 451, 425, 408, 391, 357, 329. Anal. (C$_{32}$H$_{24}$N$_4$O$_5$) C, H, N.

Example 16

Synthesis of bis(4-flourophenyl)carbonate (21)

Reaction of 4-fluorophenol with 4-fluorophenylchloroformate in pyridine/CH$_2$Cl$_2$ as described earlier afforded carbonate 21 after silica column chromatography in 85% yield as a white solid: TLC (100% CHCl$_3$) 0.7; mp 122–123° C.; IR (KBr) 3130, 3091, 1885, 1764, 1649, 1610, 1508, 1304, 1234, 1176, 1094, 1010, 902, 838, 729, 576, 510 cm$^{-1}$; $^1$H NMR (CDCl$_3$) δ 7.24 (dd, 4H, J=9.05, 4.44 Hz), 7.08 (dd, 4H, J=8.89, 8.09 Hz); $^{13}$C NMR (CDCl$_3$) δ 161.93, 159.50, 152.34, 147.06, 147.03, 122.61, 122.53, 116.60, 116.36; MS m/e (EI$^+$, relative intensity, %) 250 (M$^+$, 82) 206 (27), 178 (12), 177 (43), 139 (11), 112 (25), 111 (20), 95 (100), 83 (32), 75 (19), 57 (17).

Example 17

Synthesis of 2,5-bis[4-(N-(4-fluoro) phenoxycarbonyl)amidinophenyl]furan (8)

To a suspension of bis-amidine 1 (0.5 g, 0.0026 mol) in DMF (10 mL) at room temperature, was added a solution of carbonate 21 (0.87 g, 0.0035 mol). The resulting solution was stirred for 16 h. Ice water (40 mL) was added to the mixture and filtered, washed with water (3×30 mL), ether (30 mL) and dried in vacuum for 24 h to furnish 4-fluorophenylcarbanate 8 (0.92 g, 61%) as a yellow solid: TLC (R$_f$) 0.45 (CHCl$_3$, MeOH, NH$_4$OH, 4:1:0.2, v/v); mp>300° C.; IR (KBr) 3465–3000, 1667, 1621, 1491, 1260, 1187, 1139, 1078, 969, 859, 793, 665 cm$^{-1}$; $^1$H NMR (DMSO-d$_6$) δ 9.31 (s, 4H, D$_2$O exchangeable, NH), 8.12 (d, J=8.73 Hz, Ar—CH), 7.98 (d, 4H, J=8.57 Hz, Ar—CH), 7.33 (s, 2H, CH-furan), 7.22 (d, 8H, J=6.5 Hz, F-Ar—CH) $^{13}$C NMR (DMSO-d$_6$) δ 162.12, 161.86, 157.77, 156.53, 154.21, 153.45, 152.57, 147.76, 133.00, 132.45, 132.65, 128.79, 128.44, 127.83, 123.46, 123.38, 123.31, 115.97, 115.89, 115.60, 115.47, 115.37, 115.25; MS m/z (FAB, m-nitrobenzoic acid) 581 (M+1), 469, 443, 426, 357, 331. Anal. (C$_{32}$H$_{22}$N$_4$O$_5$F$_2$.0.5H$_2$O) C, H, N.

Example 18

Synthesis of bis(4-methoxyphenyl)carbonate (22)

Reaction of 4-methoxyphenol with 4-methoxyphenylchloroformate in pyridine/CH$_2$Cl$_2$ followed by aqueous workup as described above gave carbonate 22, after silica column chromatography, in 93% yield as a white solid: TLC (R$_f$) 0.53 (100% CHCl$_3$); mp 95° C.; IR (KBr) 3076, 2958, 2848, 1772, 1610, 1514, 1470, 1286, 1242, 1182, 1028, 894, 836, 776, 726, 534 cm$^{-1}$; $^1$H NMR (CDCl$_3$) δ 7.16 (d, 4H, J=9.05 Hz), 6.88(d, 4H, J=9.04Hz), $^{13}$C NMR (CDCl$_3$) δ 157.71, 153.04, 144.83, 121.96, 114.68, 55.80 (OCH$_3$); MS m/e (EI$^+$, relative intensity, %) 274 (M$^+$, 100), 230 (33), 215 (29), 187 (12), 124 (16), 123 (46), 107 (10), 95 (12), 77 (13), 64 (7), 52 (5), 41 (6).

Example 19

Synthesis of 2,5-bis[4-(N-(4-methoxy) phenoxycarbonyl) amidinophenyl]furan (9)

To a suspension of bis-amidine 1 (0.7 g, 0.0016 mol) in DMF (10 mL) at room temperature, was added bis(4-methoxy)phenylcarbonate (1.39 g, 0.0051 mol) and stirred for 24 h. Anhydrous ether (25 mL) was then added to the precipitated product, stirred for few min and filtered, washed with ether (3×15 mL) and dried under vacuum in a dessicator for 48 h to furnish 4-methoxyphenyl carbamate 9 (0.9 g, 65%) as a yellow solid: TLC (R$_f$) 0.68 (CHCl$_3$,MeOH, NH$_4$OH, 4:1:0.2, v/v); mp>300° C.; IR (KBr) 3450–3100, 3010, 2934, 2836, 1683, 1484, 1256, 1184, 1142, 1078, 1033, 1010, 967, 928, 850, 801, 774, 753, 696, 659, 607, 583, 559, 531 cm$^{-1}$; $^1$H NMR (DMSO-d$_6$) δ 9.26 (s, 4H, NH), 8.11 (d, 4H, J=8.54 Hz, Ar—CH), 7.98 (d, 4H, J=8.53 Hz, Ar—CH), 7.34 (s, 2H, furan-CH), 7.09 (d, 4H, J=9.04 Hz, Ar—CH of Ar—OCH$_3$), 6.93 (d, 4H, J=9.03 Hz, Ar—CH of Ar—OCH$_3$), 3.75 (s, 6H, OCH$_3$); $^{13}$C NMR (DMSO-d$_6$) δ 166.62, 156.26, 152.64, 145.07, 133.03, 132.64, 128.53, 123.41, 122.66, 114.12, 110.72, 55.36. MS m/z (FAB, thioglycerol) 605 (M+1), 481, 429, 323, 303, 289, 273, 257, 247, 229. Anal. (C$_{34}$H$_{28}$N$_4$O$_7$.1. DMF) C, H, N.

Example 20

Synthesis of 1-chloroethyl-4-nitrophenylcarbonate (16)

To an ice cold solution of 4-nitrophenol (2.0 g, 0.015 mol) and triethylamine (1.6 g, 0.016 mol) (or pyridine) in CH$_2$Cl$_2$ (20 mL) at 0–5° C. was added a solution of 1-chloroethylchloroformate (2.1 g, mmol) in CH$_2$Cl$_2$ (10 mL) and stirred for 15 min and then at room temperature overnight (16 h). The mixture was extracted with CH$_2$Cl$_2$ (50 mL), aq. NaOH (0.5 N, 50 mL), sat. NaCl solution (50 mL), water (3×50 mL) and dried (Na$_2$SO$_4$). The CH$_2$Cl$_2$ solution was filtered, evaporated in a rotavapor and the residue was purified by silicagel column chromatography using chloroform (100%) as eluent to furnish pure 16 as a white solid: TLC (R$_f$) 0.75 (CHCl$_3$); mp 70–71° C. (lit.[22] 69–70° C.); IR (KBr) 3116, 3084, 2999, 2932, 2864, 2364, 2330, 1779, 1626, 1525, 1355, 1245, 1101, 914, 863, 779, 677 cm$^{-1}$; $^1$H NMR (CDCl$_3$) δ 8.31 (dd, 2H, J=5.08, 2.07 Hz, Ar—CH), 7.43 (dd, 2H, J=4.76, 2.22 Hz, Ar—CH), 6.50 (q, 1H, J=11.67 Hz, CHClCH$_3$), 1.93 (d, 3H, J=5.87 Hz); $^{13}$C NMR (CDCl$_3$) δ 155.16, 150.65, 145.94, 125.63, 121.89, 85.44, 25.34; MS m/e (EI$^+$, relative intensity) 210 (M$^+$—HCl, 4), 139 (26), 122 (13), 109 (8), 76 (13), 75 (11), 65 (27), 64 (17), 63 (100), 50 (10), 43 (13).

Example 21

Synthesis of 1-acetoxyethyl-4-nitrophenylcarbonate (17)

To a solution of 1-chloroethyl-4-nitrophenyl carbonate (2.0 g, 0.0082 mol) in glacial acetic acid (50 mL) at room temperature, was added mercuric acetate (3.8 g, 0.012 m) and the mixture was stirred for 40 h. Water (100 mL) was then added to the mixture and extracted with ether (2×75 mL). The ethereal phase was washed with aq. NaOH (0.5 N, 30 mL), sat. NaCl (30 mL), water (2×50 mL) and dried (anhy. Na$_2$SO$_4$). The solution was filtered, concentrated in a rotavap and purified by silica gel column chromatography to afford pure 1-acetoxyethyl-4-nitrophenyl carbonate (17) (1.9 g, 89%) as a colorless liquid: TLC (R$_f$) 0.65 (CHCl$_3$); IR (film) 1779 (OCOO), 1749 (CH$_3$COO), 1615, 1592, 1528, 1491, 1266, 1110, 1070, 857 cm$^{-1}$; $^1$H NMR (CDCl$_3$) δ 8.29 (d, 2H, J=9.05 Hz, Ar—CH), 7.41 (d, 2H, J=9.04 Hz, Ar—CH), 6.84 (q, 1H, J=10.95 Hz, CH(Oac)CH$_3$), 2.14 (s, 3H, COCH$_3$), 1.62 (d, 3H, 5.4 Hz, CHCH$_3$); $^{13}$C NMR (CDCl$_3$) δ 169.09, 155.33, 150.70, 145.76, 125.52, 121.94, 92.47 (CHOAc), 20.96 (COCH$_3$), 19.61 (CHCH$_3$); MS m/e (EI$^+$, relative intensity) 210 (M$^+$—AcOH, 3), 166 (4), 122 (5), 87 (33), 63 (6), 50 (3), 43 (100).

Example 22

Synthesis of 2,5-bis[4(1-acetoxyethoxycarbonyl) amidinophenyl]furan (10)

A mixture of bis-amidine 1 (0.4 g, 0.0013 mol), diisopropylethylamine (0.35 g, 0.0026 mol) and THF/CH$_3$CN (1:1 mixture, 15 mL) was stirred at room temperature. A solution of 1-aceoxyethyl-4-nitrophenyl carbonate (0.71 g, 0.00264 mol) in THF (5 mL) was then added and continued stirring for 24 h. Solvents were removed in a rotavapor under reduced pressure at 40° C., triturated with anhy. ether (20 mL), filtered, washed with ether (2×25 mL), dried in air and crystallized from CHCl₃ether to yield 1-acetoxyethyl carbamate (10) as a yellow solid in 71% yield (0.52g): TLC ($R_f$) 0.5 (CHCl₃,MeOH,NH₄OH, 4:1:0.2, v/v); mp 165–167° C. dec; IR (KBr) 3690–2900 (br), 3458 (s), 3324 (s), 3131 (s), 2945 (s), 1734, 1667, 1640, 1607, 1562, 1488, 1412, 1362, 1279, 1243, 1147, 1117, 1089, 1057, 1022, 992, 932, 885, 842, 797, 597, 566 cm⁻¹; ¹H NMR (DMSO-d₆) δ 9.33 (s, 4H, NH), 8.09 (d, 4H, J=8.54 Hz, Ar—CH), 7.96 (d, 4H, J=8.54 Hz, Ar—CH), 7.34 (s, 2H, CH-furan), 6.79 (q, 2H, J=10.87 Hz, CHOAc), 2.03 (s, 6H, CH₃), 1.55 (d, 6H, J=5.39 Hz, CHCH₃); ¹³C NMR (DMSO-d₆) δ 168.93, 166.84, 161.49, 152.65, 133.06, 132.58, 128.59, 123.42, 110.82, 89.18, 20.82, 19.63 (CH₃); MS m/z (FAB, thioglycerol) 565 (M+1), 479, 461, 435, 375, 357, 331, 314, 288, 271. Anal. (C₂₈H₂₈N₄O₉) C, H, N.

Example 23

Synthesis of 2,5-bis[4(N-ethoxycarbonyloxy) amidinophenyl]furan (11): NaOH method To a suspension of the bis-amidoxime (2,5-bis[4-(N-hydroxy)amidinophenyl]furan) (0.86 g, 0.0028 mol) and CH₂Cl₂ (15 mL), a solution of ethylchloroformate (1.22 g, 0.011 mol) in CH₂Cl₂ (15 mL) was added and stirred for 10 min. Aq. NaOH (1 N, 12 mL) was then added dropwise and stirred at room temperature for 6 h. Ice water (10 mL) was added, filtered, washed with plenty of water (3×30 mL), dried in air and crystallized from ethanol to give pure ethyl carbonate (11) (0.67 g, 50% yield) as a white solid.

Example 24
Synthesis of ethyl 4-nitrophenylcarbonate (13) :Carbonate Method

Reaction of 4-nitrophenol with ethylchloroformate in pyridine/CH₂Cl₂ as described earlier, gave carbonate 2 as colorless crystals in 92% yield by chromatographic purification and 82% by crystallization methods. TLC ($R_f$) 0.48 (100% CHCl₃); mp 70–71° C.; IR (KBr) 3124, 3092, 3010, 2920, 2866, 1772, 1622, 1600, 1536, 1278, 1112, 1060, 1006, 908, 860, 774, 732, 662, 527, 502 cm⁻¹; ¹H NMR (CDCl₃) δ 8.29 (d, 2H, J=9.05 Hz, Ar—CH), 7.38 (d, 2H, J=9.05 Hz, Ar—CH), 4.36 (q, 2H, OCH₂, J=14.28 Hz), 1.38 (t, 3H, J=7.07 Hz, CH₃); ¹³C NMR (CDCl₃) δ 155.84, 152.65, 145.64, 125.48, 121.98, 65.74, 14.35; MS m/e (EI⁺, relative intensity, %) 212 (M⁺, 1.4), 211 (1), 139 (100), 109 (60), 89 (100), 93 (13), 81 (11), 65 (21), 63 (13).

Reaction of bis-amidoxime with ethyl 4-nitrophenyl carbonate in DMF at room temperature gave bis-ethoxycarbonyloxy derivative in 85% yield as a white solid. The physical data or compound 11 obtained by both methods were virtually identical. TLC ($R_f$) 0.5 (CHCl₃,MeOH, NH₄OH, 4:1:0.2, v/v); mp>300° C. dec.; IR (KBr) 3700–3100, 3056, 2989, 2937, 2915, 2890, 1770, 1668, 1635, 1481, 1414, 1370, 1266, 1208, 1124, 1035, 1013, 939, 857, 834, 775, 686 cm⁻¹; ¹H NMR (DMSO-d₆) δ 7.91 (d, 4H, J=7.21 Hz, Ar—CH), 7.78 (d, 4H, J=7.20 Hz, Ar—CH), 7.24 (s, 2H, CH-furan), 6.89 (s, 4H, NH), 4.20 (q, 4H, J=14 Hz, NOCOOCH₂), 1.26 (t, 6H, J=7.1 Hz, CH₃); ¹³C NMR (DMSO-d₆) δ 156.0 (OCOO), 153.48, 152.43, 131.63, 130.17, 127.29, 123.33, 109.70, 63.56, (OCH₂), 14.20 (OCH₂CH₃); MS m/z (FAB, thioglycerol) 481 (M+1), 429, 393, 377, 347, 323, 305, 288, 271, 237. Anal. (C₂₄H₂₄N₄O₇) C, H, N.

In the specification, and examples there have been disclosed typical preferred embodiments of the invention and, although specific terms are employed, they are used in a generic and descriptive sense only and not for the purposes of limitation, the scope of the invention being set forth in the following claims.

TABLE 1

In vivo Activity of Carbamate and Carbonate Prodrugs of 2,5-Bis(4-amidinophenyl)furan vs. *Pneumocystis carinii*

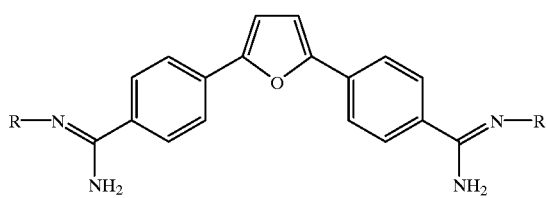

| Compound | R | Dosage[a] (μmol/kg/day) | Cysts/g of lung[a] (% of control) | Toxicity[a] |
|---|---|---|---|---|
| Saline | | — | 100.0[b] ± 13.24 | 0 |
| Pentamidine | | iv @ 22.0 | 3.06 ± 0.90 | ++ |
| 1 | H | iv @ 13.3 | 0.83 ± 0.36 | 0 |
| | | Oral @ 39.8 | 44.52 ± 13.30 | 0 |
| 2[c] | 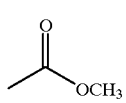 | iv @ 22.0 | 6.91 ± 6.01 | 0 |
| | | Oral @ 33.0 | 49.68 ± 20.50 | 0 |
| 3[d] | 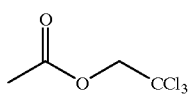 | iv @ 22.0 | 1.85 ± 1.79 | 0 |
| | | Oral @ 33.0 | 8.59 ± 9.14 | 0 |

TABLE 1-continued

| # | Structure | Dose | Result | Tox |
|---|---|---|---|---|
| 4 | CH3-C(=O)-S-Et | iv @ 22.0<br>Oral @ 33.0 | 83.01 ± 43.65<br>19.52 ± 14.22 | 0<br>0 |
| 5[c] | benzyl acetate | iv @ 11.0<br>Oral @ 33.0 | 0.03 ± 0.02<br>18.09 ± 9.16 | 0<br>0 |
| 6[d] | (5-methyl-2-oxo-1,3-dioxol-4-yl)methyl acetate | iv @ 22.0<br>Oral @ 33.0 | 0.02 ± 0.01<br>18.73 ± 11.87 | 0<br>0 |
| 7 | phenyl acetate | iv @ 22.0<br>Oral @ 33.0 | 3.61 ± 1.80<br>5.70 ± 5.15 | 0<br>0 |
| 8[d] | 4-fluorophenyl acetate | iv @ 22.0<br>Oral @ 33.0 | 0.02 ± 0.01<br>2.21 ± 0.33 | 0<br>0 |
| 9[d] | 4-methoxyphenyl acetate | iv @ 22.0<br>Oral @ 33.0 | 0.02 ± 0.01<br>2.10 ± 2.08 | 0<br>0 |
| 10[c] | ethylidene diacetate | iv @ 11.0<br>Oral @ 33.0 | 1.21 ± 1.02<br>57.16 ± 10.19 | ++<br>0 |
| 11[c] | methyl ethyl carbonate | iv @ 34.7<br>Oral @ 33.0 | 1.66 ± 0.58<br>96.90 ± 48.48 | 0<br>0 |

Elemental Analysis Data

| Compound # | Formula | Calcd for C | Calcd for H | Calcd for N | Found for C | Found for H | Found for N |
|---|---|---|---|---|---|---|---|
| 2 | $C_{20}H_{20}N_4O_5$ | 62.84 | 4.80 | 13.33 | 63.01 | 4.74 | 13.20 |
| 3 | $C_{24}H_{18}N_4O_5Cl_{16}$ | 41.70 | 3.20 | 8.11 | 41.54 | 3.01 | 8.28 |
| 4 | $C_{24}H_{24}N_4O_3S_2 \cdot 0.25H_2O$ | 59.42 | 5.09 | 11.55 | 59.26 | 4.98 | 11.29 |
| 5 | $C_{34}H_{28}N_4O_5 \cdot 2H_2O$ | 67.09 | 5.30 | 9.21 | 66.67 | 4.99 | 9.24 |
| 5M | $C_{34}H_{28}N_4O_5 \cdot 2C_4H_4O_4$ | 62.68 | 4.51 | 6.96 | 62.71 | 4.47 | 7.04 |
| 6 | $C_{30}H_{24}N_4O_{11}$ | 58.44 | 3.92 | 9.09 | 58.40 | 4.00 | 9.09 |
| 7 | $C_{32}H_{24}N_4O_5 \cdot 1.3H_2O$ | 67.67 | 4.72 | 9.87 | 67.29 | 4.53 | 10.35 |
| 8 | $C_{32}H_{22}N_4O_5F_2 \cdot 0.5H_2O$ | 65.12 | 4.10 | 9.51 | 64.82 | 4.20 | 10.03 |
| 9 | $C_{34}H_{28}N_4O_7 \cdot DMF$ | 65.57 | 5.21 | 10.33 | 67.44 | 5.19 | 10.17 |
| 10 | $C_{28}H_{28}N_4O_9$ | 59.57 | 5.00 | 9.93 | 59.41 | 5.06 | 9.82 |
| 11 | $C_{24}H_{24}N_4O_7$ | 60.00 | 5.04 | 11.66 | 59.67 | 4.95 | 11.46 |

That which is claimed:

1. A compound represented by the formula (I):

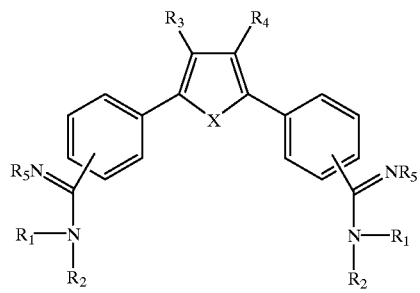

wherein:

X may be O or S;

$R_1$ and $R_2$ are may be independently selected from the group consisting of H, loweralkyl, oxyalkyl, alkoxyalkyl, cycloalkyl, aryl, hydroxyalkyl, aminoalkyl, and alkylaminoalkyl;

$R_3$ and $R_4$ are each independently selected from the group consisting of H, loweralkyl, halogen, oxyalkyl, oxyaryl, and oxyarylalkyl;

$R_5$ is represented by a formula selected from the group consisting of:

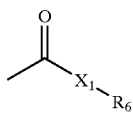 and 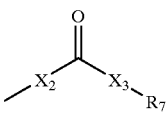

wherein:

$X_1$, $X_2$, and $X_3$ are independently selected from O and S; and $R_6$ and $R_7$ are independently selected from the group consisting of loweralkyl, aryl, alkylaryl, oxyaryl, and oxyalkyl;

or a pharmaceutically acceptable salt thereof.

2. The compound according to claim 1, wherein $R_6$ and $R_7$ are independently selected from the group consisting of: $CH_3$, $CH_2CCl_3$, $CH_2CH_3$,

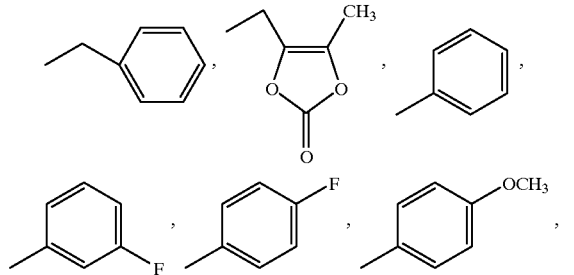

and

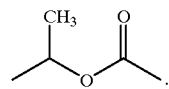

3. The compound according to claim 1, wherein each of the substituents present on the compound of formula (I) represented by the formula:

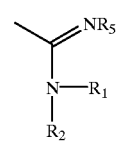

are present on the para positions of the aromatic groups on formula (I).

4. A pharmaceutical composition comprising the compound as defined by claim 1 and a pharmaceutically acceptable carrier.

5. The composition according to claim 4, wherein $R_6$ and $R_7$ are independently selected from the group consisting of: $CH_3$, $CH_2CCl_3$, $CH_2CH_3$,

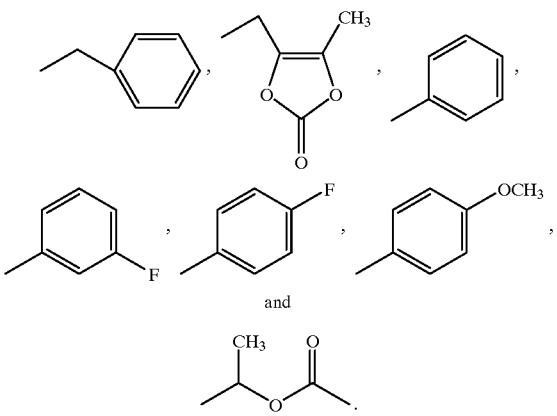

6. The composition according to claim 4, wherein each of the substituents present on the compound of formula (I) represented by the formula:

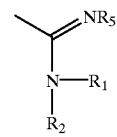

are present on the para positions of the aromatic groups on formula (I).

* * * * *

UNITED STATES PATENT AND TRADEMARK OFFICE
CERTIFICATE OF CORRECTION

PATENT NO.     : 6,486,200 B1
DATED          : November 26, 2002
INVENTOR(S)    : David W. Boykin et al.

It is certified that error appears in the above-identified patent and that said Letters Patent is hereby corrected as shown below:

Title page,
Item [60], Related U.S. Application, replace "Provisional application No. 60/142,829" with -- Provisional application No. 60/142,826 --.

Signed and Sealed this

Twenty-fifth Day of March, 2003

JAMES E. ROGAN
*Director of the United States Patent and Trademark Office*